(12) United States Patent
Keirn

(10) Patent No.: US 6,530,895 B1
(45) Date of Patent: Mar. 11, 2003

(54) OXYGENATING APPARATUS, METHOD FOR OXYGENATING A LIQUID THEREWITH, AND APPLICATIONS THEREOF

(75) Inventor: William S. Keirn, Columbia City, IN (US)

(73) Assignee: Life International Products, Inc., Naples, FL (US)

( * ) Notice: Subject to any disclaimer, the term of this patent is extended or adjusted under 35 U.S.C. 154(b) by 0 days.

(21) Appl. No.: 09/491,495

(22) Filed: Jan. 25, 2000

(51) Int. Cl.$^7$ ............................................. A61M 37/00
(52) U.S. Cl. ..................................... 604/24; 210/198.1
(58) Field of Search .................. 604/24; 210/198.1, 210/739, 192, 86, 759, 629, 96.1; 422/29 R; 261/64 R; 435/243; 241/18

(56) References Cited

U.S. PATENT DOCUMENTS

| | | | |
|---|---|---|---|
| 3,674,216 A | * | 7/1972 | Blair ............................ 241/18 |
| 4,226,719 A | | 10/1980 | Woltman ....................... 210/220 |
| 4,246,111 A | * | 1/1981 | Savard et al. ............... 210/96.1 |

(List continued on next page.)

FOREIGN PATENT DOCUMENTS

| | | | | |
|---|---|---|---|---|
| DE | 2447337 | 4/1976 | | |
| DE | 19827613 | 5/1999 | | |
| DE | 29823335 | 6/1999 | | |
| EP | 0244954 | 11/1987 | | |
| EP | 0322925 | 7/1989 | | |
| EP | 0555498 | 8/1993 | | |
| EP | 0847959 | 6/1998 | | |
| EP | 0900761 | 3/1999 | | |
| FR | 2238525 | 2/1975 | | |
| GB | 2077712 | 12/1981 | | |
| JP | 356015831 | * | 2/1981 | ............. B01F/5/04 |
| JP | 08155430 | 6/1996 | | |
| WO | 95/12452 | 5/1995 | | |
| WO | 99/55450 | 11/1999 | | |

OTHER PUBLICATIONS

Hydrodynamics and Gas–Liquid Mass Transfer in a Downward Venturi–Bubble Column Combination, C.L. Briens, L.X. Huynh, J. F. Large, A. Catros, J.R. Bernard, M.A. Bergougnou, Chemical Engineering Science, vol. 47, No. 13/14, pp. 3549–3556, 1992.

Hydrodynamics and Mass Transfer Characteristics of a Loop–Venturi Reactor with a Downflow Liquid Let Ejector, P.H.M.R. Cramers, A.A.C.M. Beenackers and L.L. van Dierendonck, Chemical Engineering Science, vol. 47, No. 13/14, pp. 3557–3564, 1992.

Mixing Shocks in Two–Phase Flow, Jan H. Witte, J. Fluid Mech. (1969), vol. 36, Part 4, pp. 639–655.

*Primary Examiner*—Teresa Walberg
*Assistant Examiner*—L. Fastovsky
(74) *Attorney, Agent, or Firm*—Baker & Daniels

(57) ABSTRACT

An apparatus for oxygenating a liquid, including a liquid pump, supply piping having an inlet connected to the pump and an outlet, first and second injectors and a chamber. The first injector has a liquid inlet forming a nozzle, a liquid outlet and an oxygen inlet, the first injector oxygen inlet intermediate the first injector liquid inlet and outlet, the supply piping outlet connected to the first injector liquid inlet. The second injector has a liquid inlet forming a nozzle, a liquid outlet and an oxygen inlet, the second injector oxygen inlet intermediate the second injector liquid inlet and outlet, the first injector liquid outlet in communication with the second injector liquid inlet, whereby liquid flows through the first and second injectors in series, each of the first and second injector oxygen inlets provided with a source of oxygen gas. The chamber has a liquid inlet and a liquid outlet, the second injector liquid outlet in communication with the chamber liquid inlet, whereby liquid flows through the second injector and the chamber in series. A process for enriching a liquid with oxygen is also disclosed.

46 Claims, 5 Drawing Sheets

U.S. PATENT DOCUMENTS

| | | | |
|---|---|---|---|
| 4,426,450 A | * | 1/1984 | Donofrio .................... 435/243 |
| 4,562,014 A | * | 12/1985 | Johnson .................... 261/64 R |
| 4,639,340 A | | 1/1987 | Garrett ...................... 261/36.1 |
| 4,645,603 A | * | 2/1987 | Frankl ........................ 210/629 |
| 4,648,973 A | | 3/1987 | Hultholm et al. |
| 4,695,378 A | | 9/1987 | Ackman et al. ......... 210/198.1 |
| 4,767,543 A | * | 8/1988 | Chornet et al. ............. 210/759 |
| 5,006,352 A | | 4/1991 | Zoltai et al. .................. 426/67 |
| 5,167,798 A | | 12/1992 | Yoon et al. ................. 209/170 |
| 5,167,806 A | | 12/1992 | Wang et al. ................ 210/188 |
| 5,273,664 A | * | 12/1993 | Schultz ....................... 210/759 |
| 5,302,286 A | | 4/1994 | Semprini et al. ........... 210/610 |
| 5,403,475 A | | 4/1995 | Allen |
| 5,423,979 A | | 6/1995 | Allen |
| 5,512,217 A | | 4/1996 | Batterham et al. |
| 5,667,670 A | * | 9/1997 | Drewery ...................... 210/86 |
| 5,766,490 A | | 6/1998 | Taylor et al. ............... 210/758 |
| 5,814,222 A | | 9/1998 | Zelenak et al. ............. 210/615 |
| 5,885,467 A | | 3/1999 | Zelenak et al. ............. 210/758 |
| 6,001,247 A | * | 12/1999 | Schultz ....................... 210/192 |
| 6,086,833 A | * | 7/2000 | Conners et al. ............. 422/292 |
| 6,090,294 A | * | 7/2000 | Teran et al. ................ 210/739 |
| 6,280,615 B1 | * | 8/2001 | Phillips et al. ........... 210/198.1 |

* cited by examiner

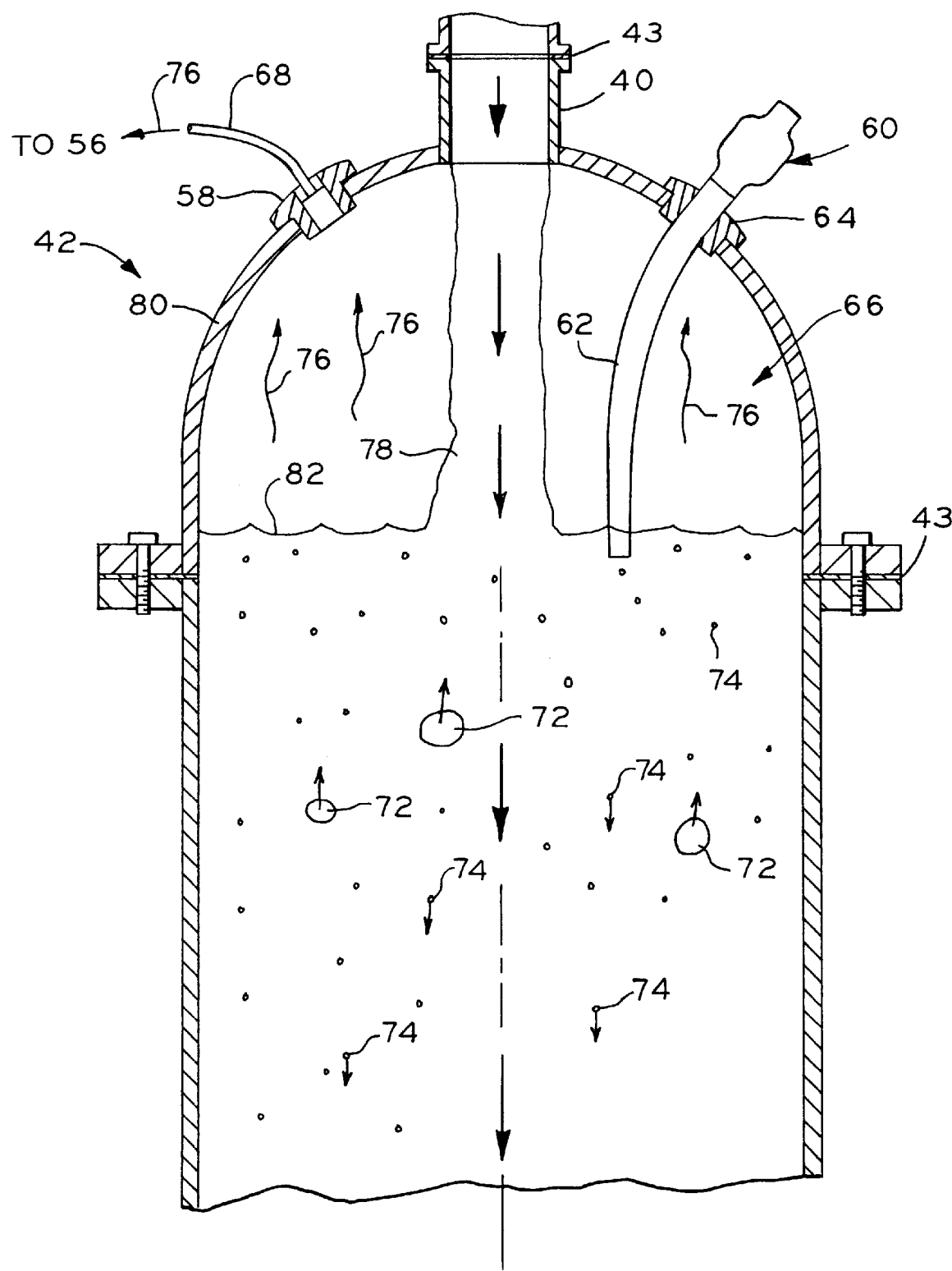
FIG_5

OXYGENATING APPARATUS, METHOD FOR OXYGENATING A LIQUID THEREWITH, AND APPLICATIONS THEREOF

BACKGROUND OF THE INVENTION

This invention relates to an apparatus for oxygenating a liquid, i.e., preparing the liquid in solution with oxygen, a method for oxygenating the liquid, and applications of liquids oxygenated by the inventive apparatus and method. The liquid to be oxygenated may be water, for example, or any of a number of other liquids.

It is known that various types of liquids are oxygenated to achieve various results. For example, consumption of an oxygen enriched beverage has a favorable effect on well-being and physical performance, for it provides oxygen to the bloodstream through the stomach lining or intestinal wall. In one case, eight test subjects of various ages and differing sex had their blood oxygen contents and their pulse rates determined. Each subject then drank between ½ and ¾ liters of highly oxygenated water. A short period after ingestion of the enriched water, evidence of a pulmonary function bypass was observed through an average blood oxygen level increase of about 30%, and the effect of a concomitant cardiac relief was observed through an average pulse rate reduction of about 10%. Further, the added oxygen tends to reduce the tartness of any carbonation and does not impart any taste to the resulting liquid.

As a further example, aerobic processes advantageously employ oxygen-containing liquids. As used throughout the specification and the claims, reference to an "aerobic" process generally includes all chemical and microbiological processes in which a chemical or microbiological process is carried out or is promoted in a liquid medium in the presence of oxygen. Suitable aerobic processes in which an oxygenated liquid can be advantageously employed include, for example, processes in which heretofore water has been aerated such as by bubbling air thereinto, and also in situ or ex situ bioremediation of contaminated (e.g., with petroleum products) or oxygen-depleted bodies of water; wastewater, sludge and animal waste treatment, both by fixed film and by suspended growth methods; rehabilitation of atrophying lakes; biological oxygen demand (BOD) reduction techniques; fresh water aquaculture (e.g., fish farming); salt water aquaculture (e.g., shrimp farming); hydroponic agriculture; odor suppression barriers for anaerobic processes; and insolubilization of dissolved contaminates (e.g., iron, and manganese ions) for removal by filtration or sedimentation.

It is also known that some fermentation processes, i.e., processes which involve fermenting a fermentation liquor, commonly employed in drug production or food processing by microorganisms, benefit from the fermentation liquor being comprised of an oxygenated liquid.

It is also known that numerous types of therapeutic processes can benefit from the use of oxygenated liquids. "Therapeutic" processes, as used throughout the specification and the claims, involve the oxygenation of the body or its parts by treatment with an agent in a liquid vehicle containing dissolved oxygen. Suitable therapeutic processes in which an oxygenated liquid can be advantageously employed include, for example, processes for increasing the oxygen content of blood and tissues; oxygenation of wounds to increase the rate of healing and to reduce infections; oxygenated organ transplant storage media; tumor oxygenation for radiation therapy and chemotherapy; lung bypass by oxygenated liquids in case of pulmonary deficiencies; treatment for carbon monoxide poisoning; mouthwashes, dentifrices; topical, including cosmetic treatment media; contact lens treating solutions; and cell level therapeutic applications.

Moreover, it is known that oxygenated liquids can be advantageously employed as solvents for physiological saline isotonic solutions, especially when kept in sealed, sterile containers. Such saline solutions may be prepared by dissolving a sodium concentrate into an oxygen enriched liquid. Alternatively, prepared saline solutions may themselves be subjected to the oxygenation process. Oxygenated saline solutions can provide a more direct and efficient way of providing oxygen to the bloodstream than having the oxygen absorbed thereinto through the stomach lining or intestinal wall, as is done through consumption of an oxygenated beverage.

As a further example, oxygenated liquids may be advantageously employed in some disinfection processes. Such disinfection processes are those in which a very high level of dissolved oxygen serves to kill microbial life in the same manner as does chlorine or ozone. These oxygen concentration levels would exceed those resulting after dilution in a biomass for aerobic treatment thereof as described above. For example, it was found that bacteria in a petri dish was killed when merely subjected to oxygen-enriched water having a dissolved oxygen level of about 50 to 70 mg/l. It has also previously been speculated that rather than subjecting certain microbial life to a disinfectant comprising an oxygenated liquid, a disinfection process may instead involve oxygenating a liquid contaminated with microbial life, whereby the disinfection would take place during the oxygenation process.

Regardless of the use to which oxygenated liquids are put, means for achieving increased levels of dissolved oxygen in a liquid efficiently is desirable, as are means for doing so at high rates of production.

Currently, among the most effective methods and apparatuses for saturating a liquid with oxygen on an industrial scale are those disclosed in U.S. Pat. No. 5,766,490, issued Jun. 16, 1998, and entitled "Oxygenating Apparatus, Method For Oxygenating Water fan Therewith, and Applications Thereof", which is expressly incorporated herein by reference, and in U.S. Pat. No. 6,120,008, issued Sep. 19, 2000, and entitled "Oxygenating Apparatus, Method For Oxygenating a Liquid Therewith, and Applications Thereof", which is also expressly incorporated herein by reference.

According to the process disclosed by U.S. Pat. No. 5,766,490, a sealed enriching space is provided which includes a venturi mixer through which liquid to be oxygenated upwardly flows, the oxygen gas introduced to the liquid in the venturi throat. This method and apparatus works well, producing an oxygen-enriched liquid having at least 40 mg/l of dissolved oxygen at a rate of approximately 50,000 gallons per day (gpd), but does not take full advantage of the mixing potential offered by a venturi mixer or injector.

According to the process disclosed by U.S. Pat. No. 6,120,008, a sealed enriching space is provided which includes a single venturi mixer through which liquid to be oxygenated flows downwardly, the oxygen gas introduced to the liquid in the venturi throat. The pressure of the liquid/ oxygen admixture is raised as it flows through a diffuser as it exits the venturi, whereby the buoyancy of the oxygen bubbles therein is increased. These large bubbles float upwards against the downward admixture flow and are broken up into smaller bubbles by a shock wave established in the diffuser by the high rate of liquid flow therethrough. The smaller bubbles are more readily absorbed into the admixture. This method and apparatus works well, producing an oxygen enriched liquid having 160 mg/l oxygen at a rate of approximately 100,000 gpd.

A method and apparatus for producing an oxygen enriched liquid having even greater oxygen concentrations than may be achieved through prior apparatuses and processes is desirable, particularly where the higher oxygen concentrations is realized in a liquid post-process at atmospheric pressure.

Further, an apparatus which may be easily cleaned in place by providing a reverse flow of a cleaning liquid therethrough, which is particularly useful in liquid food preparation environments, is also desirable.

SUMMARY OF THE INVENTION

Throughout the specification, drawings and the claims, "water" is meant to include any still or effervescent liquid intended to be enriched with oxygen, and "liquid" is meant to include water and any other still or effervescent liquid that is capable of super oxygenation, including flavored water and other ingestive beverages, and saline solutions.

Objects of the present invention include enabling the production of a liquid enriched with dissolved oxygen at higher oxygen concentrations, particularly at atmospheric pressure, than has been possible through apparatuses and processes according to the prior art, and to do so at industrial scale, continuous production rates.

Another object of the present invention is to provide improved aerobic, therapeutic and fermentation processes, and saline solutions, employing liquids highly enriched with oxygen in accordance with the present invention.

The present invention provides an apparatus for oxygenating a liquid, including a liquid pump, supply piping having an inlet connected to the pump and an outlet, first and second injectors and a chamber. The first injector has a liquid inlet forming a nozzle, a liquid outlet and an oxygen inlet, the first injector oxygen inlet intermediate the first injector liquid inlet and outlet, the supply piping outlet connected to the first injector liquid inlet. The second injector has a liquid inlet forming a nozzle, a liquid outlet and an oxygen inlet, the second injector oxygen inlet intermediate the second injector liquid inlet and outlet, the first injector liquid outlet in communication with the second injector liquid inlet, whereby liquid flows through the first and second injectors in series, each of the first and second injector oxygen inlets provided with a source of oxygen gas. The chamber has a liquid inlet and a liquid outlet, the second injector liquid outlet in communication with the chamber liquid inlet, whereby liquid flows through the second injector and the chamber in series.

The present invention also provides a process for enriching a liquid with oxygen, which includes the steps of: (a) introducing a liquid under pressure into a first injector and flowing the liquid downwardly through the first injector; (b) introducing oxygen into the liquid as it flows through the first injector to mix the liquid and oxygen; (c) introducing the admixture of liquid and oxygen resulting from the step (b) under pressure into a second injector and flowing the liquid downwardly through the second injector; (d) introducing oxygen into the admixture as it flows through the second injector to further mix the liquid and oxygen; (e) introducing the admixture of liquid and oxygen resulting from step (d) into a chamber, wherein undissolved oxygen is released from the admixture introduced into the chamber and is collected in the chamber; and (f) recovering an oxygen enriched liquid from the chamber.

The present invention also provides a physiological saline solution which includes as the solvent an oxygen enriched liquid, the liquid having an oxygen concentration level of at least about 160 mg/l. The present invention also provides a process of preparing a physiological saline solution which includes the steps of: providing an oxygen enriched liquid having an oxygen concentration level of at least about 160 mg/l; and dissolving a sodium concentrate into the oxygen enriched liquid.

The present invention involves processes for using oxygen enriched liquid prepared in accordance with the preparatory process of the present invention and by the use of the apparatus of the invention. These processes of use include aerobic, disinfection, therapeutic and fermentation processes advantageously employing oxygen-containing liquids, as described above.

If desired, liquids treated in accordance with the present invention can also be made effervescent by the addition of a gas such as carbon dioxide. If carbon dioxide is added after the dissolution of the oxygen in the water, then it will displace a portion of the dissolved oxygen. It has been found, however, that an effervescent liquid can be further enriched with oxygen to a substantial degree after the addition of the carbon dioxide. Even more oxygen can be dissolved in the liquid if the liquid being enriched with the oxygen is chilled at the time of the oxygen enrichment. To an even greater extent than achievable by chilling the liquid, the solubility of oxygen in a liquid may be increased by increasing the pressure of the liquid and oxygen admixture.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 5 is a fragmentary sectional side view of the debubbler chamber of the apparatus of FIG. 1.

Figure 1:
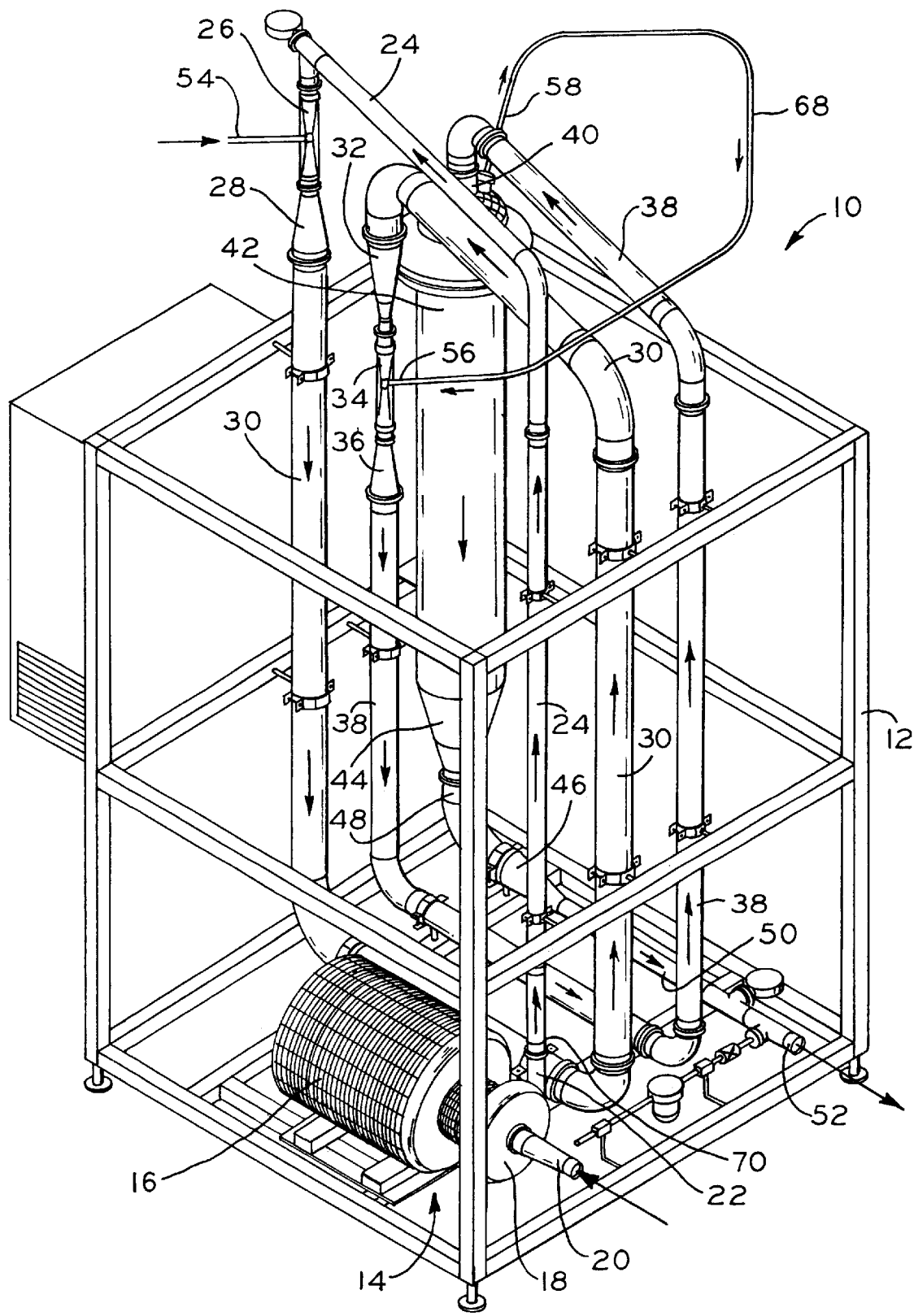
FIG. 1 is a first perspective view of one embodiment of an apparatus according to the present invention.

Corresponding reference characters indicate corresponding parts throughout the several views. Although the drawings represent embodiments of the present invention, the drawings are not necessarily to scale and certain features may be exaggerated or simplified in order to better illustrate and explain the present invention. The exemplifications set out herein illustrate embodiments of the invention in alternative forms, and such exemplifications are not to be construed as being exhaustive or to limit the scope of the invention in any manner.

DETAILED DESCRIPTION OF THE INVENTION

Figure 2:
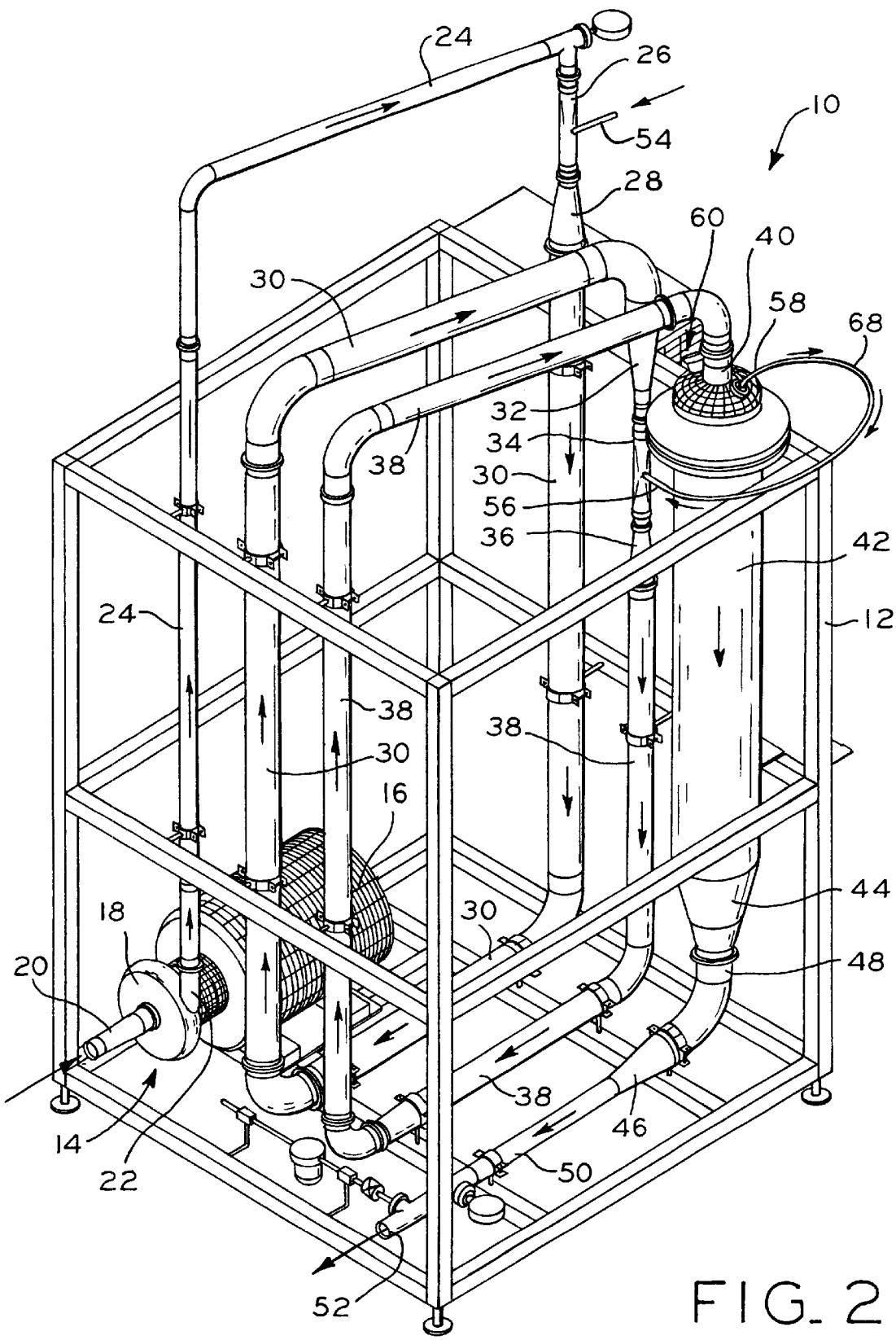
FIG. 2 is a second perspective view of the apparatus of FIG. 1.
Figure 3:
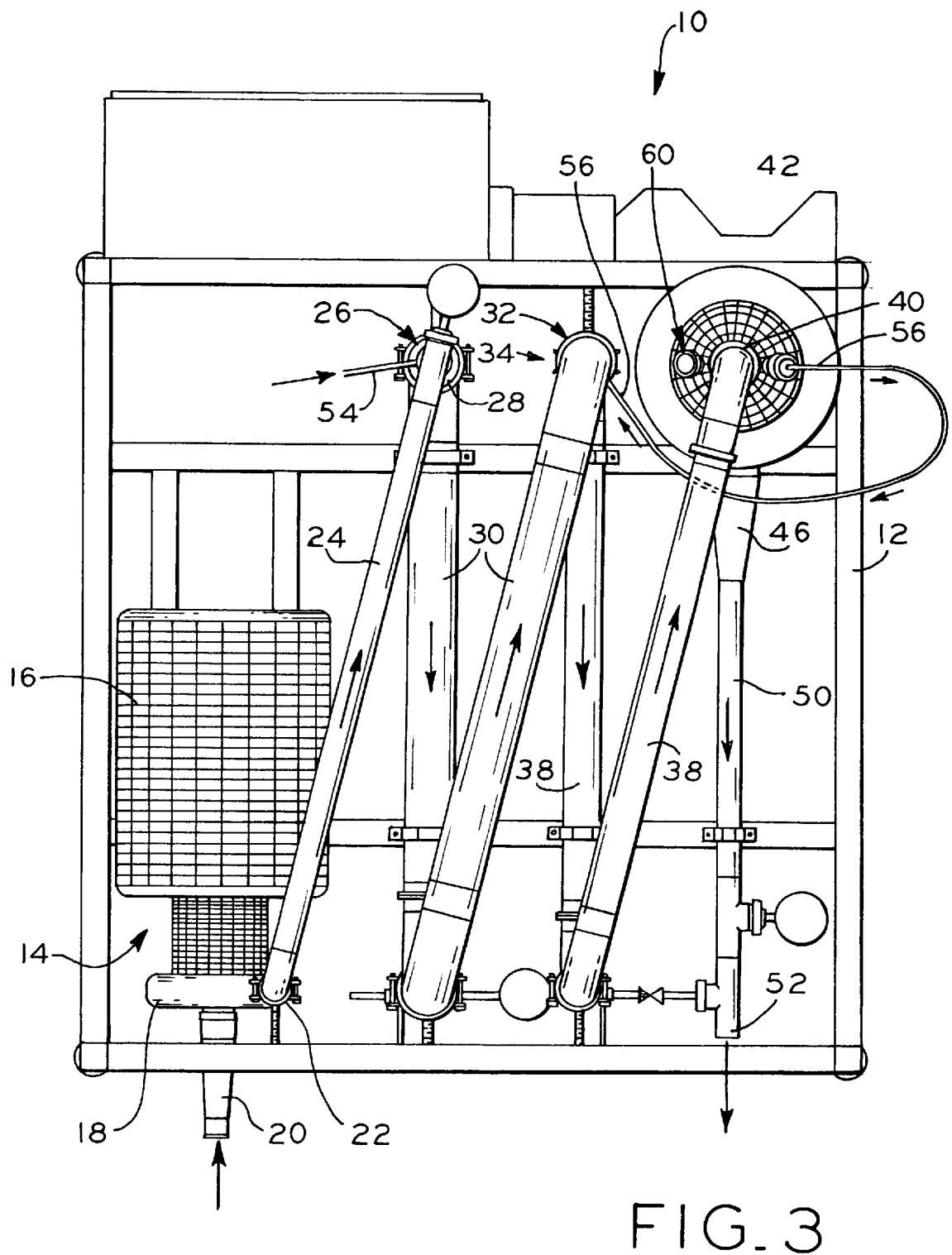
FIG. 3 is a plan view of the apparatus of FIG. 1.
Figure 4:
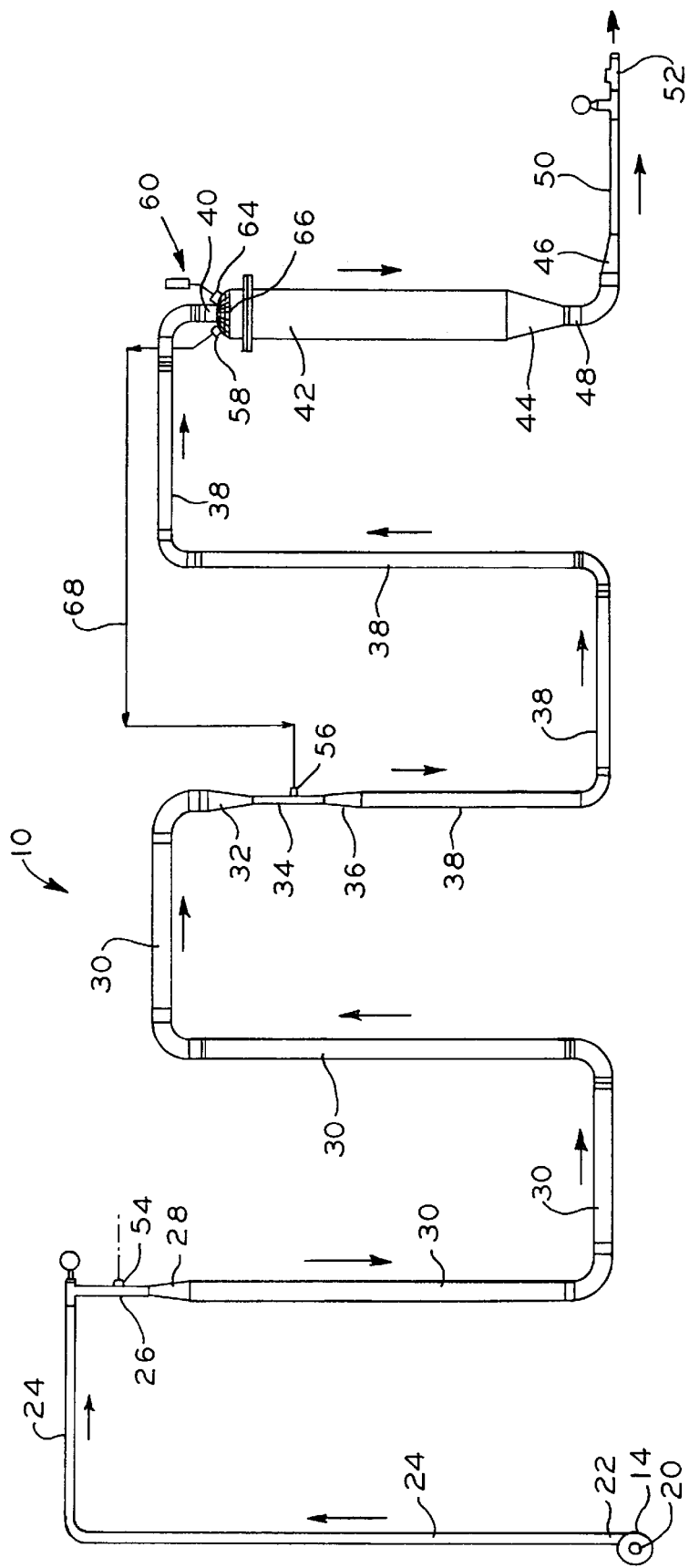
FIG. 4 is a schematic view of the apparatus of FIG. 1.

FIGS. 1–4 illustrate oxygenating apparatus 10, one embodiment of an apparatus according to the present invention. Apparatus 10 comprises frame 12 which forms a parallelepiped. Within frame 12 is mounted pump assembly 14 which comprises electric motor 16 and centrifugal pump 18. Motor 16 may be a 20 horsepower, 3-phase electric motor which rotates at a speed of 3500 rpm. Pump 18 may be Model SSV manufactured by Goulds Pumps and directly driven by motor 16. The liquid to be enriched with oxygen is supplied to inlet 20 of the centrifugal pump 18 and is forced under pressure from outlet 22 of the pump and through supply piping 24. Supply piping 24 is two inch outside diameter stainless steel 316L. The liquid forced from the pump is initially conveyed vertically upward through supply piping 24, and then downward to the inlet of first injector 26. First injector 26 is a venturi-type injector having a nozzle for an inlet and a diffuser for an outlet, with a throat disposed between the inlet and outlet; oxygen gas is provided to the gas inlet at the throat as described further hereinbelow. First injector 26 may be, for example, Mazzei Model No. 1584. The outlet of the first injector is fitted to the inlet of first diffuser/expander 28, the outlet of which is fitted to first interconnecting conduit 30. Notably, in apparatus 10 the inlet of first injector 26 is approximately 10 feet 7 inches above the floor on which the apparatus sits. First interconnecting conduit 30 is four inch outside diameter stainless steel 316L.

The liquid and oxygen are introduced and mixed within first injector 26; the admixture then continues downward and then vertically upward through first interconnecting conduit 30, and then downward to the inlet of first nozzle/reducer 32. The unlabeled arrows depicted in the drawings indicate the flow of liquid through apparatus 10. The outlet of first nozzle/reducer 32 is fitted to the inlet of second injector 34. Second injector 34 may be identical to or similar to first injector 26, having a nozzle for an inlet and a diffuser for an outlet. It is to be noted that both first and second injectors 26, 34, respectively, are each substantially vertically oriented such that the liquid flow therethrough is downward.

The outlet of second injector 34 is fitted to the inlet of second diffuser/expander 36, the outlet of which is fitted to second interconnecting conduit 38. Second interconnecting conduit 38 is three inch outside diameter stainless steel 316L. As will be discussed further hereinbelow, the liquid and oxygen admixture which is provided to the inlet of second injector 34 is further mixed with additional oxygen in the second injector. Downstream of the second injector the admixture, now containing additional oxygen, is directed downward through second interconnecting conduit 38 and then vertically upward through conduit 38, and then downward to inlet 40 at the top of debubbler chamber 42. Debubbler chamber 42 is ten inch outside diameter stainless steel 316L and is approximately six feet in length. Notably, the joints between the interconnected piping, conduits, injectors, reducers, expanders and the debubbler chamber may be provided with Teflon seals 43, which are of the type preferably used in food production environments, for such seals are resistant to absorption of food substances. Alternatively, other types of suitable seals may be used.

The admixture of liquid and oxygen flows slowly downward through debubbler chamber 42 and through second nozzle/reducer 44 which comprises the lowermost portion of chamber 42. The inlet of third nozzle/reducer 46 is connected to outlet 48 of second nozzle/reducer 44. The outlet of third nozzle/reducer 46 is attached to the inlet of outlet conduit 50, which is two inch outside diameter stainless steel 316L.

Valve means are provided in outlet conduit 50 to provide the appropriate internal pressure within debubbler chamber 42, the supply piping and the conduits of apparatus 10 as described further hereinbelow; the oxygenated liquid recovered from outlet 52 of conduit 50, which may be remote from apparatus 10, is at substantially atmospheric pressure (1 atm or 14.7 psia).

Oxygen gas inlet 54 of first injector 26 is attached to a source of oxygen gas which may be, for example, a container of compressed oxygen provided with a pressure regulator (not shown), the container and regulator attached to frame 12 and comprising apparatus 10. Alternatively, the source of pressurized oxygen may be external to apparatus 10. Oxygen outlet fitting 58, provided in top portion 66 of debubbler chamber 42, is connected to one end of return line 68; the other end of return line 68 is fitted to oxygen gas inlet 56 of second injector 34. Oxygen gas available in the top portion of chamber 42, above the liquid level therein, is provided to gas inlet 56 of the second injector. The flow of liquid through the throat of second injector 34 establishes a vacuum at oxygen inlet 56, which draws the available oxygen gas from the top portion of chamber 42. Moreover, as described further hereinbelow, the oxygen gas located in top portion 66 of chamber 42 is under pressure, and is thus urged through return line 68 to injector 34.

Referring now to FIG. 5, it can be seen that liquid level control valve 60, comprising downwardly depending tube 62, is attached to fitting 64 provided in the top wall portion of debubbler chamber 42. Tube 62 of level control valve 60 extends downwardly from fitting 64 into the interior of the debubbler chamber; the free end of tube 62 is located approximately ten to twelve inches below fitting 64 and ordinarily extends below the liquid level in the chamber. The purpose of level control valve 60 is to maintain a minimum height of liquid and oxygen admixture within debubbler chamber 42 by relieving excessive oxygen gas buildup in the chamber, which might otherwise force the liquid level in the chamber downward. Should the level of the admixture be forced downward under the influence of oxygen gas pressure in the top portion of chamber 42 to a level below the terminal or free end of tube 62, oxygen gas will be vented to atmosphere through level control valve 60, thereby relieving the pressure on the surface of the admixture, and allowing it to rise.

Notably, oxygen outlet 58 is disposed well above the free end of tube 62, and during normal operation of apparatus 10, with the surface level of the liquid within the debubbler chamber at a height above the free end of tube 62, oxygen under pressure is urged through outlet 58 and oxygen return line 68 to second injector 34. This recirculated oxygen is again introduced into the liquid and oxygen admixture in second injector 34, thereby continuously providing oxygen to the process by which the liquid is thoroughly enriched with oxygen.

In operation, centrifugal pump 18 provides a flow of 70 gallons per minute (gpm) of liquid at approximately 130 psig to the inlet of first injector 26. Oxygen gas is provided at approximately 50 cubic feet per hour at 70 psig to oxygen inlet 54 of first injector 26. The oxygen pressure at inlet 56 of second injector 34 is unregulated, and is received at whatever flow rate is available. It is to be noted, however, that the minimum pressure of the liquid in chamber 42 is regulated by valve means at outlet 52 of apparatus 10. Thus, in conjunction with level control valve 60, an oxygen gas pressure of approximately 85 psig, which is substantially equivalent to that of the liquid discharge pressure from the apparatus, is maintained in top portion 66 of chamber 42.

Further, unlike the absorber disclosed in above-mentioned U.S. Pat. No. 6,120,008, debubbler chamber 42 is not provided merely to provide increased residence time for the oxygen in the admixture, during which the oxygen is allowed to be further absorbed into the admixture. Rather, the sole intended function of the debubbler chamber, through which the liquid slowly flows downward, is to allow a considerable period of time for undissolved gases or large bubbles 72 (FIG. 5) to remove themselves from the admixture, to thereby avoid the nucleating of small bubbles 74 when large bubbles 72 would otherwise pass over some downstream anomaly within and outside of apparatus 10; such an anomaly would create a pressure shear through which large bubbles 72 would tend to absorb small bubbles 74. The direction in which bubbles 72 and 74 flow are indicated by the arrows individually associated therewith in FIG. 5. It can be seen that small bubbles 74 flow with the liquid through chamber 42, whereas large bubbles 72 float upwards, against the flow of liquid in the chamber. Thus, in the debubbler chamber, large bubbles 72 are provided a means to exit the admixture and oxygen 76 from those large bubbles is recirculated to second injector 34, where it is reintroduced to the liquid stream. This process continues until the admixture exiting the debubbler chamber comprises only fine bubbles of oxygen in liquid; the absence of large bubbles reduces the likelihood of the small bubbles being nucleated as they experience an anomaly within or outside of apparatus 10.

Additionally, as the liquid and oxygen admixture is introduced into chamber 42 through its inlet 40, via flow stream 78, the admixture tumbles through pure oxygen gas 76 which is collected in upper portion 66 of the chamber, between upper wall 80 of the chamber and surface level 82 of the admixture within the chamber. The effect of the liquid tumbling through the pure oxygen in the top of the chamber provides internal aeration of the liquid under pressure and further contributes to the absorption of oxygen by the liquid. The cushion of pure oxygen in top portion 66 of debubbler chamber 42 is not critical to the inventive process, although it is estimated that the abovementioned internal aeration provides an additional one to two percent, by weight, of total oxygen to the admixture recovered from apparatus 10.

Important to the inventive process is that the volume of debubbler chamber 42 is large enough to provide a slow flow velocity therethrough, thereby providing ample time for removal of the bulk of undissolved gases 72 from the admixture therein. The goal is to slow the flow velocity of the liquid admixture flowing through the debubbler chamber to sufficiently allow gases 72 to remove themselves from the liquid through surface 82 of the liquid admixture. Thus the diameter of chamber 42 is substantially larger than the conduits and supply piping of apparatus 10. Those skilled in the art will now appreciate that the inventive process purges large oxygen bubbles 72 from the admixture within chamber 42, and that if large bubbles 72 were allowed to remain in the admixture they would attract small bubbles 74 as the large bubbles pass a pressure shear downstream of the debubbler chamber, internal or external to apparatus 10, resulting in the nucleation of the small bubbles into the large bubbles and the removal of the small bubbles from the admixture.

The process of the present invention yields an oxygen-enriched liquid received from outlet 52, at atmospheric pressure, which has a dissolved oxygen level of at least about 160 mg/l at a flow rate of approximately 70 gpm or approximately 100,000 gpd.

Notably, apparatus 10 contains no static or dynamic turbulent mixers in any of its conduits or the debubbler chamber, which promotes easy cleaning of apparatus 10. Such turbulent mixers may become clogged with debris or residue, depending on the nature of the liquid conveyed through the apparatus. Apparatus 10 may be cleaned in place by reversely flushing the apparatus with a cleaning liquid, which may be pure water or an appropriate solution. This is done by providing a flow of the cleaning liquid into apparatus outlet 52 and allowing the cleaning liquid to reversely flow through the debubbler chamber, the conduits and supply piping, and the injectors. The cleaning liquid exits apparatus 10 through inlet 70 of the supply piping which is, during cleaning, disconnected from outlet 22 of pump 18.

While this invention has been described as having a particular design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An apparatus for oxygenating a liquid, comprising:
   a liquid pump;
   supply piping having an inlet connected to said pump and an outlet;
   a first injector having a liquid inlet forming a nozzle, a liquid outlet and an oxygen inlet, said first injector oxygen inlet intermediate said first injector liquid inlet and outlet, said supply piping outlet connected to said first injector liquid inlet;
   a second injector having a liquid inlet forming a nozzle, a liquid outlet and an oxygen inlet, said second injector oxygen inlet intermediate said second injector liquid inlet and outlet, said first injector liquid outlet in communication with said second injector liquid inlet, whereby liquid flows through said first and second injectors in series, each of said first and second injector oxygen inlets provided with a source of oxygen gas;
   a chamber having a liquid inlet and a liquid outlet, said second injector liquid outlet in communication with said chamber liquid inlet, whereby liquid flows through said second injector and said chamber in series, said chamber containing a quantity of oxygen gas, at least a portion of said quantity of oxygen gas from said chamber being provided to said oxygen inlet of one of said first and second injectors; and
   an outlet conduit, said outlet conduit having an inlet connected to said chamber liquid outlet and an outlet from which oxygenated liquid exits said apparatus.

2. The apparatus of claim 1, wherein said first injector oxygen inlet is fluid communication with a pressurized container of oxygen.

3. The apparatus of claim 2, wherein said apparatus comprises said pressurized container of oxygen.

4. The apparatus of claim 1, further comprising a first interconnecting conduit, and wherein said first injector outlet and said second injector liquid inlet are connected through said first interconnecting conduit.

5. The apparatus of claim 4, wherein said supply piping has a cross sectional size which is smaller than a cross sectional size of said first interconnecting conduit.

6. The apparatus of claim 4, further comprising a second interconnecting conduit, and wherein said second injector liquid outlet and said chamber liquid inlet are connected through said second interconnecting conduit.

7. The apparatus of claim 6, wherein said first interconnecting conduit has a cross sectional size which is larger than a cross sectional size of said second interconnecting conduit.

8. The apparatus of claim 6, further comprising an outlet conduit, said outlet conduit having an inlet connected to said chamber liquid outlet and an outlet from which oxygenated liquid exits said apparatus.

9. The apparatus of claim 1, wherein said outlet of said outlet conduit is open to substantially atmospheric pressure.

10. The apparatus of claim 1, wherein said chamber is elongate and has a longitudinal axis, and liquid flows through said chamber substantially along said longitudinal axis.

11. The apparatus of claim 1, wherein said chamber is provided with an oxygen gas outlet, said chamber oxygen outlet in communication with said second injector oxygen inlet.

12. The apparatus of claim 11, wherein said chamber contains both a quantity of oxygenated liquid and a quantity of oxygen gas, said quantity of oxygen gas including oxygen not dissolved into said quantity of oxygenated liquid.

13. The apparatus of claim 12, wherein a surface exists in said chamber between said quantity of oxygenated liquid and said quantity of oxygen gas, a portion of the oxygen in said quantity of oxygenated liquid moved from one side of said surface to the other side of said surface, said portion of oxygen absorbed into said quantity of oxygen gas.

14. The apparatus of claim 1, wherein liquid flowing through said supply piping has a first flow velocity and liquid flowing through said chamber has a second flow velocity, said second flow velocity substantially less than said first flow velocity.

15. The apparatus of claim 14, wherein liquid flowing through said supply piping has a first volumetric flow rate and liquid flowing through said chamber has a second volumetric flow rate, said first and second volumetric flow rates substantially equivalent.

16. The apparatus of claim 15, wherein said first and second volumetric flow rates are about 70 gpm.

17. The apparatus of claim 1, further comprising an oxygenated liquid outlet open to atmospheric pressure and through which oxygenated liquid exits said apparatus, said oxygenated liquid outlet in communication with said chamber liquid outlet, oxygenated liquid recovered from said oxygenated liquid outlet having a dissolved oxygen level of at least about 160 mg/l at 1 atm.

18. The apparatus of claim 1, wherein each of said first and second injectors is oriented such that its respective said liquid inlet is above its respective said liquid outlet, whereby liquid flow through said first and second injectors is generally downward.

19. The apparatus of claim 18, wherein each of said first and second injectors is located at a substantially elevated position relative to said chamber liquid outlet.

20. The apparatus of claim 1, wherein said chamber liquid inlet is above said chamber liquid outlet, whereby liquid flow through said chamber is generally downward.

21. The apparatus of claim 1, wherein said first and second injectors each comprise a venturi having a throat, each said injector oxygen inlet communicating with a said venturi throat.

22. The apparatus of claim 21, wherein each said venturi comprises a diffuser having an inlet and an outlet, said diffuser inlet adjacent said venturi throat.

23. A fermentation process which comprises fermenting a fermentation liquor comprising an oxygen-enriched liquid prepared by the apparatus of claim 1 and by a process including introducing a liquid under pressure, introducing oxygen and recovering oxygen.

24. An aerobic process which comprises carrying out one of a chemical and a microbiological reaction in a liquid comprising an oxygen-enriched liquid prepared by the apparatus of claim 1 and by a process including introducing a liquid under pressure, introducing oxygen and recovering oxygen.

25. A therapeutic process which comprises carrying out a therapeutic treatment of a body with an agent comprising an oxygen-enriched liquid prepared by the apparatus of claim 1 and by a process including introducing a liquid under pressure, introducing oxygen and recovering oxygen as a vehicle.

26. A process for bottling a potable beverage which comprises introducing a beverage comprising an oxygen-enriched liquid prepared by the apparatus of claim 1 and by a process including introducing a liquid under pressure, introducing oxygen and recovering oxygen into a container, and sealing said container.

27. A process of preparing a physiological saline solution which comprises the steps of: providing oxygen enriched liquid prepared by the apparatus of claim 1; and dissolving a sodium concentrate into said oxygen enriched liquid.

28. A disinfection process which comprises subjecting microbial life to a liquid comprising an oxygen-enriched liquid prepared by the apparatus of claim 1 and by a process including introducing a liquid under pressure, introducing oxygen and recovering oxygen.

29. A disinfection process which comprises enriching a liquid containing microbial life with oxygen with the apparatus of claim 1 and by a process including introducing a liquid under pressure, introducing oxygen and recovering oxygen.

30. A process for enriching a liquid with oxygen, which comprises the steps of:

(a) introducing a liquid under pressure into a first injector and flowing the liquid downwardly through the first injector;

(b) introducing oxygen into the liquid as it flows through the first injector to mix the liquid and oxygen;

(c) introducing the admixture of liquid and oxygen resulting from said step (b) under pressure into a second injector and flowing the liquid downwardly through the second injector;

(d) introducing oxygen into the admixture as it flows through the second injector to further mix the liquid and oxygen;

(e) introducing the admixture of liquid and oxygen resulting from said step (d) into a chamber, wherein undissolved oxygen is released from the admixture introduced into the chamber and is collected in the chamber; and (f) recovering an oxygen enriched liquid from the chamber.

31. The process of claim 30, wherein said recovering step comprises recovering an oxygen enriched liquid having a dissolved oxygen level of at least about 160 mg/l from the chamber.

32. The process of claim 31, wherein the recovered oxygen enriched liquid has a dissolved oxygen level of at least about 160 mg/l at about 1 atm pressure.

33. The process of claim 30, wherein said step (e) further comprises flowing the admixture of liquid and oxygen downwardly through the chamber.

34. The process of claim 30, wherein the liquid is introduced into the first injector at a first volumetric flow rate and oxygenated liquid is recovered from the chamber at a second volumetric flow rate, the first and second volumetric flow rates substantially equivalent.

35. The process of claim 34, wherein the first and second volumetric flow rates are each about 70 gpm.

36. The process of claim 34, further comprising the step of flowing liquid to the first injector at a first velocity, and flowing liquid through the chamber at a second velocity, the first velocity substantially greater than the second velocity.

37. The process of claim 30, further comprising the step of removing oxygen which has collected in the chamber, and wherein the oxygen introduced into the second injector includes oxygen removed from the chamber.

38. A fermentation process which comprises fermenting a fermentation liquor comprising an oxygen-enriched liquid prepared by the process of claim 30.

39. An aerobic process which comprises carrying out one of a chemical and a microbiological reaction in a liquid comprising an oxygen-enriched liquid prepared by the process of claim 30.

40. A therapeutic process which comprises carrying out a therapeutic treatment of a body with an agent comprising an oxygen-enriched liquid prepared by the process of claim 30 as a vehicle.

41. A process for bottling a potable beverage which comprises introducing a beverage comprising an oxygen-enriched liquid prepared by the process of claim 30 into a container, and sealing said container.

42. A process of preparing a physiological saline solution which comprises the steps of: preparing an oxygen enriched liquid in accordance with the process of claim 30; and dissolving a sodium concentrate into said oxygen enriched liquid.

43. A disinfection process which comprises subjecting microbial life to a liquid comprising an oxygen-enriched liquid prepared by the process of claim 30.

44. A disinfection process which comprises enriching a liquid containing microbial life with oxygen by the process of claim 30.

45. A physiological saline solution which comprises as the solvent an oxygen enriched liquid, said liquid having an oxygen concentration level of at least about 160 mg/l.

46. A process of preparing a physiological saline solution which comprises the steps of: providing an oxygen enriched liquid having an oxygen concentration level of at least about 160 mg/l; and dissolving a sodium concentrate into said oxygen enriched liquid.

* * * * *